United States Patent [19]

Nakamura et al.

[11] Patent Number: 5,221,750
[45] Date of Patent: Jun. 22, 1993

[54] 2-ARYL-4-ISOXAZOLIN-3-ONE DERIVATIVES

[75] Inventors: Koki Nakamura; Shigeru Nakamura, both of Kanagawa, Japan

[73] Assignee: Fuji Photo Film Co., Ltd., Kanagawa, Japan

[21] Appl. No.: 819,661

[22] Filed: Jan. 13, 1992

Related U.S. Application Data

[63] Continuation of Ser. No. 519,346, May 1, 1990, abandoned, which is a continuation of Ser. No. 152,721, Feb. 5, 1988, abandoned.

[30] Foreign Application Priority Data

Feb. 5, 1987 [JP] Japan ................. 62-25442

[51] Int. Cl.⁵ .......................... C07D 261/12
[52] U.S. Cl. ....................... 548/243; 430/380; 544/137; 548/366.1; 548/369.1; 564/87; 564/442; 568/29; 568/44
[58] Field of Search .......................... 548/243

[56] References Cited

U.S. PATENT DOCUMENTS

| | | | |
|---|---|---|---|
| 3,119,832 | 1/1964 | Matter et al. | 548/243 |
| 4,490,462 | 12/1984 | Kawaguchi et al. | 430/543 |
| 4,692,182 | 9/1987 | Chang | 548/243 |
| 4,783,396 | 11/1988 | Nakamura et al. | 430/353 |
| 4,886,736 | 12/1989 | Nakamura et al. | 548/243 |

FOREIGN PATENT DOCUMENTS

| | | | |
|---|---|---|---|
| 46-31856 | 9/1971 | Japan | 548/243 |
| 104274 | 8/1980 | Japan . | |

OTHER PUBLICATIONS

Nakamura et al., Chemical Abstracts, vol. 110, No. 95215 (1989) (Abstract for JP 63/192761 (Aug. 10, 1988).
Nakamura et al. Chemical Abstracts, vol. 110, No. 135226 (1989) (Abstract for JP 63/192760 (Aug. 10, 1988).
Abstract for JP 46/31856 (Sep. 17, 1971).
Kishida et al., Chemical Abstracts, vol. 75, No. 140825v (1971).
Hirai et al., Chemical Abstracts, vol. 109, No. 83528 (1988) for JP 62/244044, Oct. 24, 1987.
Nakamura eta l., Chemical Abstracts, vol. 109, No. 180480 (1988) for JP 62/245256 Oct. 26, 1987.

Primary Examiner—Emily Bernhardt
Attorney, Agent, or Firm—Sughrue, Mion, Zinn, Macpeak & Seas

[57] ABSTRACT

2-aryl-4-isoxazolin-3-1-derivatives of formula (I), useful as intermediates for positive working compounds in silver halide photographic materials

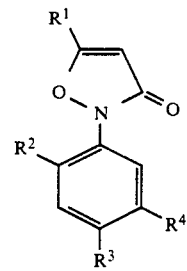

wherein $R^1$ represents a substituted or unsubstituted alkyl having from 1 to 6 carbon atoms or a substituted or unsubstituted aryl having from 6 to 24 carbon atoms; and $R^2$, $R^3$, and $R^4$, are the same or different, each having up to 20 carbon atoms and each represents hydrogen, a substituted or unsubstituted alkoxy, a substituted or unsubstituted aryloxy, a substituted or unsubstituted acyl, a substituted or unsubstituted alkoxycarbonyl, a substituted or unsubstituted aryloxycarbonyl, halogen, nitro, a substituted or unsubstituted carbamoyl, a substituted or unsubstituted sulfamoyl, a substituted or unsubstituted sulfonyl, cyano, or trifluoromethyl, with the proviso that at least one of said $R^2$ and $R^3$ is cyano, a substituted or unsubstituted sulfonyl, trifluoromethyl, or nitro.

10 Claims, No Drawings

2-ARYL-4-ISOXAZOLIN-3-ONE DERIVATIVES

This is a continuation of application Ser. No. 07/519,346, filed May 1, 1990, now abandoned, which is a continuation of application Ser. No. 07/152,721, filed Feb. 5, 1988, now abandoned.

FIELD OF THE INVENTION

This invention relates to 2-aryl-4-isoxazolin-3-one derivatives, and more particularly to 2-arylisoxazolin-3-one derivatives useful as intermediates for positive working compounds in silver halide photographic materials. These derivatives are also useful as physiologically active materials.

BACKGROUND OF THE INVENTION

Various 2-arylisoxazolin-3-one derivatives and synthesis methods thereof are described in Heterocycles, 20(6), 1123-1126(1983), Chemical and Pharmaceutical Bulletin, 30(9), 3097-3105, Heterocycles, 19(3), pages 515-520, Heterocycles, 19(3), pages 521-524, Journal of Heterocyclic Chemistry, 17(4), 727-731, Chemical and Pharmaceutical Bulletin, 19(7), 1389-1394, Japanese Patent Application (OPI) No. 104274/80 (the term "OPI" as used herein means an "unexamined published application"), Chemical Abstracts, Vol. 74, No. 17, 87947p, ibid., Vol. 75, No. 23, 140824v, ibid., Vol. 76, No. 23, 140775a, ibid., Vol. 97, No. 19, 16296u, etc.

However, 2-arylisoxazolin-3-one derivatives wherein the substituent at the 2-position of the isoxazolin nucleus is an aryl group substituted by an electron attractive group(s) having a higher electron attractive property than a chlorine group have never been known.

SUMMARY OF THE INVENTION

An object of this invention is, therefore, to provide a 2-aryl-4-isoxazolin-3-one derivative wherein the isoxazoline nucleus is substituted at the 2-position thereof by an aryl group containing an electron attractive group(s) having a higher electron attractive property than a chlorine group.

That is, the invention is concerned with a 2-aryl-4-isoxazolin-3-one derivative represented by formula (I)

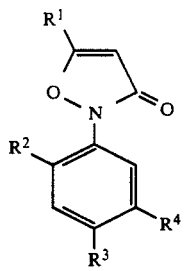

wherein $R^1$ represents an alkyl group which may be substituted or an aryl group which may be substituted; and $R^2$, $R^3$, and $R^4$, which may be the same or different, each represents a hydrogen atom, an alkoxy group which may be substituted, an aryloxy group which may be substituted, an acyl group which may be substituted, an alkoxycarbonyl group which may be substituted, an aryloxycarbonyl group which may be substituted, a halogen atom, a nitro group, a carbamoyl group which may be substituted, a sulfamoyl group which may be substituted, a sulfonyl group which may be substituted, a cyano group, or a trifluoromethyl group, with the proviso that at least one of $R^2$ and $R^3$ is a cyano group, a sulfonyl group which may be substituted, a trifluoromethyl group, or a nitro group.

DETAILED DESCRIPTION OF THE INVENTION

In formula (I) described above, $R^1$ is an alkyl group which may be substituted (e.g., a methyl group, an ethyl group, an isopropyl group, a cyclohexyl group, a t-butyl group, a chloromethyl group, an N-methylacetylaminomethyl group, an octylthiomethyl group, an adamantyl group, an undecyl group, a heptadecyl group, etc.) or an aryl group which may be substituted (e.g., a phenyl group, a 2-methylphenyl group, a 4-methylphenyl group, a 4-methoxyphenyl group, a 3-methoxy-4-acetamidophenyl group, a 4-dodecyloxyphenyl group, a 4-octadecyloxyphenyl group, a 3-sulfo-4-methoxyphenyl group, etc.). Among these groups, alkyl groups having from 1 to 6 carbon atoms and aryl groups having from 6 to 24 carbon atoms are preferred.

In formula (I), $R^2$, $R^3$, and $R^4$ each is an alkoxy group or aryloxy group either of which may be substituted (e.g., a methoxy group, a 2-methoxyethoxy group, a phenoxy group, a 4-n-hexadecylcarbamoylphenoxy group, an ethoxy group, a n-hexyloxy group, a n-hexadecyloxy group, a methoxypropyl group, etc.), an acyl group which may be substituted (e.g., an acetyl group, a n-dodecanoyl group, a benzoyl group, a 2-ethoxycarbonylbenzoyl group, a 2,2-dimethylpropanoyl group, etc.), an alkoxycarbonyl group or aryloxycarbonyl group, either of which may be substituted (e.g., a methoxycarbonyl group, an ethoxycarbonyl group, a n-octyloxycarbonyl group, a n-hexadecyloxycarbonyl group, a phenoxycarbonyl group, etc.), a sulfonyl group which may be substituted (e.g., a methylsulfonyl group, a chloromethylsulfonyl group, an ethylsulfonyl group, a n-dodecylsulfonyl group, a n-tetradecylsulfonyl group, a phenylsulfonyl group, a 4-methylphenylsulfonyl group, a t-dodecylsulfonyl group, etc.), a carbamoyl group which may be substituted (e.g., a carbamoyl group, a dimethylcarbamoyl group, a diethylcarbamoyl group, a n-butylcarbamoyl group, a 3-(2,4-di-t-pentylphenoxy)propylcarbamoyl group, an N-methyl-N-n-octylcarbamoyl group, a (3-hexadecylsulfamoyl)-phenylcarbamoyl group, an N-methyl-N-n-octadecylcarbamoyl group, a n-hexadecylcarbamoyl group, a 3-n-dodecyloxypropylcarbamoyl group, etc.), a sulfamoyl group which may be substituted (e.g., a methylsulfamoyl group, a dimethylsulfamoyl group, a diethylsulfamoyl group, a dibutylsulfamoyl group, an N-methyl-N-n-hexylsulfamoyl group, an N-methyl-N-n-octylsulfamoyl group, an N-methyl-N-n-hexadecylsulfamoyl group, an N-methyl-N-n-octadecylsulfamoyl group, a n-dodecylsulfamoyl group, an N-phenyl-N-hexadecylsulfamoyl group, an N-methyl-N-3-methoxypropylsulfamoyl group, a bis(2-methoxyethyl)sulfamoyl group, etc.), a nitro group, a cyano group, a halogen atom, or a trifluoromethyl group, with the proviso that at least one of $R^2$ and $R^3$ is a nitro group, a cyano group, a sulfonyl group or a trifluoromethyl group as a group having a higher electron attractive property than a chlorine group.

In this invention, compounds wherein at least one of $R^2$ and $R^3$ is a nitro group or a sulfonyl group are preferred, and compounds wherein at least one of $R^2$ and $R^3$ is a nitro group are particularly preferred.

Also, the compound of formula (I) described above wherein one of $R^2$ and $R^3$ is a nitro group and the other of $R^2$ and $R^3$ and/or $R^4$ is a sulfonyl group, a sulfamoyl group, an alkoxycarbonyl group, a carbamoyl group, an acyl group, a trifluoromethyl group, or a cyano group is also preferred.

Furthermore, the compound of formula (I) wherein $R^2$ is a nitro group, $R^3$ is a sulfamoyl group, a carbamoyl group, an alkoxycarbonyl group, or a trifluoromethyl group, and $R^4$ is a hydrogen atom is particularly preferred.

The compound of this invention shown by formula (I) described above can be generally synthesized by following method [A] or [B].

Method [A]

A method of obtaining the 4-isoxazolin-3-one derivative by N-acylating a nitrogen-substituted hydroxylamine with a propionic acid derivative (ester or acid halide) and ring-closing the N-acylated product under basic conditions (examples of the method are described in *Chemical Abstracts*, Vol. 76, No. 23, 140775a, ibid., Vol. 75, No. 17, 110227k, etc.) or a method of obtaining the 4-isoxazolin-3-one derivative by N-acylating a nitrogen-substituted hydroxylamine with a diketene or a β-keto-acid derivative and performing the dehydration ring-closure of the N-acylated product (examples of the method are described in *Heterocycles*, Vol. 20, No. 6, pages 1123–1126, ibid., Vol. 19, No. 3, pages 521–524, etc.).

Method [B]

A method of obtaining the 4-isoxazolin-3-one derivative by performing the displacement reaction of an aromatic compound active to aromatic nucleophilic displacement, such as a benzene having an electron attractive group at the 2-position or conjugated position thereof, and 3-hydroxyisoxazole in an aprotic polar solvent such as dimethyl sulfoxide or dimethylformamide under basic conditions.

Specific examples of the compound of this invention shown by formula (I) are shown as follows together with the particular synthesis methods suitable for producing them, but the invention is not limited by the following examples:

| No. | Compound | Melting piont (°C.) | Synthesis method |
|---|---|---|---|
| (1) | (structure with t-$C_4H_9$, $O_2N$, $SO_2N(CH_3)_2$) | 167~168 | [B] |
| (2) | (structure with t-$C_4H_9$, $O_2N$, $SO_2N(C_2H_5)_2$) | 87~88 | [B] |
| (3) | (structure with t-$C_4H_9$, $O_2N$, $SO_2NHC_{16}H_{33}$) | 97~98 | [B] |

| No. | Compound | Melting piont (°C.) | Synthesis method |
|---|---|---|---|
| (4) | t-C₄H₉ isoxazolone-N-(2-nitro-4-(N-methyl-N-hexadecylsulfamoyl)phenyl) | 67~68 | [B] |
| (5) | t-C₄H₉ isoxazolone-N-(2-nitro-4-(N-methyl-N-octadecylsulfamoyl)phenyl) | 68~69 | [B] |
| (6) | t-C₄H₉ isoxazolone-N-(2-nitro-4-trifluoromethylphenyl) | 116~117 | [B] |
| (7) | t-C₄H₉ isoxazolone-N-(2-nitro-4-ethoxycarbonylphenyl) | 88 | [B] |
| (8) | t-C₄H₉ isoxazolone-N-(2-nitro-4-(N-methyl-N-octadecylcarbamoyl)phenyl) | 64 | [B] |

-continued

| No. | Compound | Melting piont (°C.) | Synthesis method |
|---|---|---|---|
| (9) | t-C₄H₉ isoxazolinone with N-(2-nitro-5-hexadecyloxy-4-ethoxycarbonyl)phenyl group | 35~36 | [B] |
| (10) | t-C₄H₉ isoxazolinone with N-(4-nitrophenyl) group | 125~127 | [B] |
| (11) | t-C₄H₉ isoxazolinone with N-(2,4-dinitrophenyl) group | 167~168 | [B] |
| (12) | t-C₄H₉ isoxazolinone with N-(4-nitro-3-trifluoromethylphenyl) group | 125~126 | [B] |
| (13) | t-C₄H₉ isoxazolinone with N-(2-nitro-4-morpholinosulfonylphenyl) group | 181~182 | [B] |

-continued

| No. | Compound | Melting piont (°C.) | Synthesis method |
|---|---|---|---|
| (14) | t-C4H9 / C6H13-N(C6H13)SO2- / NO2 (isoxazolone N-aryl) | oil | [B] |
| (15) | t-C4H9 / F3C / NO2 | 59~60 | [B] |
| (16) | t-C4H9 / O2N / Cl | 132 | [B] |
| (17) | H3C / O2N / SO2N(C2H5)2 | 141~142 | [B] |
| (18) | H3C / O2N / SO2N(CH3)(C6H13) | oil | [B] |

-continued

| No. | Compound | Melting piont (°C.) | Synthesis method |
|---|---|---|---|
| (19) | 3-methyl-5-methyl-isoxazol-3(2H)-one N-substituted with 2-nitro-4-(N-methyl-N-octylsulfamoyl)phenyl | 43~44 | [B] |
| (20) | 3-methyl-5-methyl-isoxazol-3(2H)-one N-substituted with 2-nitro-4-(N-methyl-N-decylsulfamoyl)phenyl | 52 | [B] |
| (21) | 3-methyl-5-methyl-isoxazol-3(2H)-one N-substituted with 2-nitro-4-(N-methyl-N-hexadecylsulfamoyl)phenyl | 63~65 | [B] |
| (22) | 5-methyl-isoxazol-3(2H)-one N-substituted with 2-nitro-4-trifluoromethylphenyl | 122 | [B] |
| (23) | 5-methyl-isoxazol-3(2H)-one N-substituted with 2-nitro-4-ethoxycarbonylphenyl | 122~123 | [B] |

-continued

| No. | Compound | Melting piont (°C.) | Synthesis method |
|---|---|---|---|
| (24) | (structure: 5-methyl-isoxazol-3(2H)-one N-substituted with 2-nitro-4-(N-methyl-N-octadecylsulfamoyl)phenyl) | 71~72 | [B] |
| (25) | (structure: 5-methyl-isoxazol-3(2H)-one N-substituted with 2-nitro-4-(N,N-dibutylsulfamoyl)phenyl) | 84~86 | [B] |
| (26) | (structure: 5-methyl-isoxazol-3(2H)-one N-substituted with 2-nitro-4-(N,N-dioctylsulfamoyl)phenyl) | 64~65 | [B] |
| (27) | (structure: 5-t-butyl-isoxazol-3(2H)-one N-substituted with 2-($SO_2C_{14}H_{29}$)-4-($SO_2CH_3$)phenyl) | 85~86 | [B] |
| (28) | (structure: 5-t-butyl-isoxazol-3(2H)-one N-substituted with 2-($C_{10}H_{21}SO_2$)-5-($CF_3$)phenyl) | oily product (NMR data - see later) | [A] |

-continued

| No. | Compound | Melting piont (°C.) | Synthesis method |
|---|---|---|---|
| (29) | (isoxazolone with t-C$_4$H$_9$ at 5-position, N-aryl with 2-CH$_3$SO$_2$ and 4-SO$_2$CH$_3$) | 166~168 | [B] |
| (30) | (isoxazolone with C$_{11}$H$_{23}$ at 5-position, N-aryl with 2-CH$_3$SO$_2$, 4-SO$_2$CH$_3$, 5-CF$_3$) | 97~98 | [B] |
| (31) | (isoxazolone with t-C$_4$H$_9$ at 5-position, N-aryl with 2-CN and 4-SO$_2$CH$_3$) | 115~116 | [B] |
| (32) | (isoxazolone with H$_3$C at 5-position, N-aryl with 2-NO$_2$ and 4-C(O)-phenyl) | 159~160 | [B] |
| (33) | (isoxazolone with t-C$_4$H$_9$ at 5-position, N-aryl with 2-SO$_2$N(CH$_3$)(C$_{18}$H$_{37}$) and 4-NO$_2$) | 55~56 | [B] |

-continued

| No. | Compound | Melting point (°C.) | Synthesis method |
|---|---|---|---|
| (34) | t-C$_4$H$_9$ group on isoxazolone N-linked to phenyl-4-SO$_2$CH$_3$ | 130~131 | [A] |
| (35) | 5-(4-hydroxyphenyl)isoxazol-3-one, N-(2-nitro-4-methylsulfonylphenyl) | 233~234 | [B] |
| (36) | 5-(4-n-C$_{16}$H$_{32}$O-phenyl)isoxazol-3-one, N-(2-nitro-4-CF$_3$-phenyl) | 95~98 | [B] |
| (37) | 5-(4-hydroxyphenyl)isoxazol-3-one, N-(2-nitro-4-(N-methyl-N-C$_{18}$H$_{37}$-sulfamoyl)phenyl) | 208~209 | [B] |
| (38) | 5-(4-CH$_3$O-phenyl)isoxazol-3-one, N-(2-nitro-4-CF$_3$-phenyl) | 170~171 | [B] |

-continued

| No. | Compound | Melting point (°C.) | Synthesis method |
|---|---|---|---|
| (39) | (structure: n-$C_{16}H_{33}O$-phenyl-isoxazolone-N-(2-nitro-4-($SO_2N(CH_3)_2$)phenyl)) | 107~108 | [B] |
| (40) | (structure: HO-phenyl-isoxazolone-N-(2-nitro-4-($SO_2N(CH_3)_2$)phenyl)) | 242~244 | [B] |
| (41) | (structure: $CH_3CONH$-phenyl-isoxazolone-N-(2-nitro-4-$CF_3$-phenyl)) | 238~239 | [B] |
| (42) | (structure: $CH_3O$-, $SO_2N(CH_3)(C_{18}H_{37})$-phenyl-isoxazolone-N-(2-nitro-4-$SO_2N(C_2H_5)_2$-phenyl)) | 111~113 | [B] |

-continued

| No. | Compound | Melting piont (°C.) | Synthesis method |
|---|---|---|---|
| (43) | | 93~94 | [B] |
| (44) | | >260 | [B] |
| (45) | | 88~89 | [B] |
| (46) | | 97~98 | [B] |

-continued

| No. | Compound | Melting piont (°C.) | Synthesis method |
|---|---|---|---|
| (47) | | 183~185 | [B] |
| (48) | | 120~122 | [B] |
| (49) | | 238~239 | [B] |
| (50) | | 142~143 | [B] |

-continued

| No. | Compound | Melting piont (°C.) | Synthesis method |
|---|---|---|---|
| (51) | 5-phenyl-2-(2-nitro-4-trifluoromethylphenyl)isoxazol-3(2H)-one | 185~187 | [B] |
| (52) | 5-t-C$_4$H$_9$-2-(2-methylsulfinyl-4-methylthiophenyl)isoxazol-3(2H)-one (with CH$_3$SO and SOCH$_3$ substituents) | 159~160 | [A] |
| (53) | 5-t-C$_4$H$_9$-2-(2-nitro-4-methylsulfonylphenyl)isoxazol-3(2H)-one (O$_2$N, SO$_2$CH$_3$) | 163~164 | [B] |
| (54) | 5-t-C$_4$H$_9$-2-(2-methylsulfonyl-4-methylsulfonyl-5-trifluoromethylphenyl)isoxazol-3(2H)-one (CH$_3$SO$_2$, CF$_3$, SO$_2$CH$_3$) | 165~168 | [B] |
| (55) | 5-t-C$_4$H$_9$-2-[2-nitro-4-(N,N-bis(2-methoxyethyl)sulfamoyl)phenyl]isoxazol-3(2H)-one (O$_2$N, SO$_2$N(CH$_2$CH$_2$OCH$_3$)$_2$) | 103~104 | [B] |

| No. | Compound | Melting piont (°C.) | Synthesis method |
| --- | --- | --- | --- |
| (56) | H₃C group with isoxazolinone and 2-CN-4-(SO₂CH₃)phenyl substituent | 172~173 | [B] |
| (57) | CH₃O-phenyl isoxazolinone with 2-NO₂-4-(SO₂N(CH₃)₂)phenyl substituent | 193~195 | [B] |

The compounds of this invention shown by formula (I) described above are important intermediates for synthesizing a group of particularly important compounds known as positive working compounds capable of releasing photographically useful reagents by causing an oxidation-reduction reaction.

The positive working compounds prepared using the compounds of this invention as intermediate compounds have various advantages as described, for example, in Japanese Patent Application (OPI) Nos. 244044/87 and 245256/87 and U.S. application Ser. Nos. 925,350 (filed Oct. 30, 1986), now U.S. Pat. No. 4,783,396, and 65,194 (filed Jun. 12, 1987), now U.S. Pat. No. 4,886,736.

Also, the 2-aryl-4-isoxazolin-3-one derivatives have herbicidal activity and pharmacological activities as sterilizers, analgesic agents, anti-inflammatory agents, etc., and are thus important as physiologically active materials.

Then, the invention is explained more practically by the following examples.

EXAMPLE 1

Synthesis of Compound (28), 5-t-butyl-2-(2-dodecylsulfonyl-5-trifluoromethylphenyl)-4-isoxazolin-3-one by Method [A]:

Synthesis Example 1-1

Synthesis of 3-t-butyl-5-pyrazolidone:

In 2.5 liters of ethanol was dissolved 1.0 kg of ethyl pivaloylacetate and 320 g of hydrazine hydrate was added dropwise to the solution under water-cooling. Thereafter, the reaction was performed overnight at room temperature and then 5.0 liters of water was added to the reaction mixture followed by stirring. Crystals thus deposited were recovered by filtration under reduced pressure, washed well with water, then washed with a small amount of methanol, and air-dried. Thus, 812 g of the above-described compound was obtained with a yield of 98.5%.

Synthesis Example 1-2

Synthesis of 4,4-dibromo-3-t-butyl-5-pyrazolidone:

In 2 0 liters of acetic acid was dissolved 658 g of 3-t-butyl-5-pyrazolidone prepared above and 1.5 kg of bromine was added dropwise to the solution under water-cooling with stirring. Thereafter, the reaction was performed overnight and then 5.0 liters of water was added to the reaction mixture. Crystals deposited were recovered by filtration under reduced pressure, washed well with water, then washed with a small amount of methanol, and air-dried. Thus, 1.36 kg of the above-described compound was obtained with a yield of 97.2%.

Synthesis Example 1-3

Synthesis of 4,4-dimethyl-2-pentiolic acid:

In 3.0 liters of water was dissolved 552 g of sodium hydroxide and the solution was cooled below 5° C. by adding ice thereto. Then, 4,4-dibromo-3-t-butyl-5-pyrazolidone prepared above was added gradually to the solution with stirring while keeping the temperature thereof below 5° C. In this case, when the temperature raised, acetonitrile was added to the solution for preventing defoaming of ice. After the reaction was over, the reaction mixture was acidified with 6N hydrochloric acid and the reaction product was extracted twice with the addition of ethyl acetate.

The extract formed was collected and dried over anhydrous sodium sulfate and the ethyl acetate was distilled off under reduced pressure. The oil obtained as the residue was 4,4-dimethyl-2-pentiolic acid. The oil was used in the following reaction without being purified.

Synthesis Example 1-4

Synthesis of 4,4-dimethyl-2-pentiolic acid chloride:

A mixture of 466 g of 4,4-dimethyl-2-pentiolic acid obtained in the above step and 3.5 liters of methylene chloride was stirred, 483 g of thionyl chloride was added to the mixture, and after performing the reaction for one hour, the reaction mixture was refluxed, whereby hydrogen chloride gas generated vigorously. After refluxing the reaction mixture for 2 hours, the solvent was evaporated off and the residue was distilled under reduced pressure to provide 290 g of the desired product as a colorless liquid having a boiling point of about 70° C./20 mmHg. The yield was 54.3%.

Synthesis Example 1-5

Synthesis of 4-decylthio-3-nitrobenzotrifluoride:

After mixing 56.4 g of 4-chloro-3-nitrobenzotrifluoride, 44 g of decylmercaptane, 50 g of sodium methoxide, and 300 ml of methanol, the reaction was performed for 5 hours at 80° C. After cooling, the reaction mixture was poured into ice-water and crystals thus deposited were recovered by filtration to provide 88.0 g of the desired product with a yield of 96.9%.

Synthesis Example 1-6

Synthesis of 4-decylsulfonyl-3-nitrobenzotrifluoride:

After adding 1 g of sodium tungstenate to a mixture of 86 g of 4-decylthio-3-nitrobenzotrifluoride obtained in the above step and 300 ml of acetic acid, the resultant mixture was heated to 70° C. Then, 46 ml of an aqueous 35% hydrogen peroxide solution was added dropwise to the mixture while maintaining it at 80° to 85° C. Thereafter, the reaction was performed for 6 hours at the same temperature. After the reaction was over, water was added to the reaction mixture and crystals thus deposited were recovered by filtration and dried to provide 93.1 g of the desired product with a yield of 99.3%.

Synthesis Example 1-7

Synthesis of 4-decylsulfonyl-3-hydroxyaminobenzotrifluoride:

After mixing 100 g of 4-decylsulfonyl-3-nitrobenzotrifluoride obtained in the above step, 100 g of zinc powder, and 450 ml of ethanol, an aqueous 10% ammonium chloride solution was added to the mixture while maintaining the mixture at 50° to 65° C. to perform reaction. After the reaction was over, the reaction mixture was filtered by Celite to remove undissolved matters and then poured into water, and the reaction product was extracted with ethyl acetate. Then, the solvent was distilled off from the filtrate and then the residue was recrystallized from n-hexane to provide 80.2 g of the desired product with a yield of 84%.

Synthesis Example 1-8

Synthesis of Compound (28), 5-t-butyl-2-(2-decylsulfonyl-5-trifluoromethylphenyl)-4-isoxazolin-3-one:

In 80 ml of diethyl ether were dissolved 10 g of 4-decylsulfonyl-3-hydroxyaminobenzotrifluoride obtained in the above step and 4.2 g of 4,4-dimethyl-2-pentiolic acid chloride prepared in Synthesis Example 1-4 described above and after slowly adding dropwise 3.2 g of triethylamine to the solution at 0° C., the temperature of the mixture was gradually allowed to rise to room temperature. Then, after allowing the mixture to stand overnight, the solvent was distilled off from the mixture and 50 ml of methanol was added to the residue. After cooling the mixture to 0° C., 50 g of an aqueous 10% sodium hydroxide solution was added dropwise to the mixture and then the reaction was performed for one hour. After the reaction was over, the reaction mixture obtained was neutralized with diluted hydrochloric acid and the product was extracted with ethyl acetate. The organic layer formed was carefully separated by silica gel flash column chromatography, whereby 3.0 g of the desired product was obtained as an oily main product. The yield was 23.4%.

The nuclear magnetic resonance (NMR) spectra of the product obtained were as follows.

(CDCl$_3$): δ8.36 (1H, d), 7.98 (1H, dd), 7.75 (1H, d), 5.57 (1H, s), 3.43 (2H, t), 1.32 (9H, s).

|  | Elemental Analysis: | | |
|---|---|---|---|
|  | C (%) | H (%) | N (%) |
| Calcd. | 58.88 | 7.00 | 2.86 |
| Found | 58.79 | 7.20 | 2.77 |

EXAMPLE 2

Synthesis of Compound (4), 5-t-Butyl-2-(4-N-methyl-N-hexadecylsulfamoyl-2-nitrophenyl)-4-isoxazolin-3-one by Method [B]:

Synthesis Example 2-1

Synthesis of 5-t-butyl-3-hydroxyisoxazole:

In 2 liters of an aqueous 4N sodium hydroxide solution was dissolved 583.7 g of hydroxylamine hydrochloride, 2 liters of ethanol was added to the solution under ice-cooling, and then the pH thereof was adjusted to 10.0 by the addition of a 1:1 mixture of an aqueous 4N sodium hydroxide solution and ethanol. To the solution were simultaneously added dropwise 1380 g of ethyl pivaloylacetate and a 1:1 mixture of an aqueous 4N sodium hydroxide solution and ethanol so that the pH of the reaction mixture became 10±0.2 and the temperature thereof became 0° to 5° C.

Thereafter, the mixture was stirred for 2 hours at room temperature and after pouring the reaction mixture into 6 kg of concentrated hydrochloric acid at 0° C., the mixture was allowed to stand for 12 hours. Crystals thus deposited were recovered by filtration, sufficiently washed with water, and dried to provide 770 g of the above described compound with a yield of 68.2%. The melting point of the product was from 99° C. to 101° C.

Synthesis Example 2-2

Synthesis of 4-chloro-3-nitrobenzenesulfonyl chloride:

To a mixture of 1280 g of potassium 4-chloro-3-nitrobenzenesulfonate, 1150 ml of acetonitrile, 250 ml of sulforan, and 30 ml of dimethylacetamide was added dropwise 1250 ml of phosphorus oxychloride while maintaining the internal temperature thereof at 60° C. to 70° C. Then, after performing reaction for 3 hours at 73° C., the reaction mixture was cooled with water and after gradually adding thereto 400 ml of water, the reaction mixture was poured into 5 liters of ice-water. Crystals deposited were filtered by filtration, washed with water, and then dried to provide 1060 g of the above-described product with a yield of 84%. The melting point thereof was 55° C. to 56° C.

Synthesis Example 2-3

Synthesis of 4-chloro-3-nitro-N-hexadecylbenzenesulfonamide:

To 4-chloro-3-nitrobenzenesulfonyl chloride obtained in the above step was added 1 liter of dichloromethane and the mixture was cooled to 0° C. To the solution formed was added dropwise a mixture of 600 g of hexadecylamine, 251 ml of triethylamine, and 780 ml of dichloromethane at 20° C. to 30° C. After performing reaction for 2 hours at room temperature, the dichloromethane was distilled off from the reaction mixture under reduced pressure and the residue thus formed was dissolved in 3 liters of methanol under heating. The mixture was gradually cooled to deposit crystals at room temperature, 3 liters of methanol was added to the system while ice-cooling to further deposit crystals, and the crystals formed were recovered by filtration and dried to provide 1020 g of the above-described compound with a yield of 88%. The melting point thereof was 91° C. to 93° C.

Synthesis Example 2-4

Synthesis of 4-chloro-3-nitro-N-methyl-N-hexadecylbenzenesulfonamide:

In 640 ml of acetone was dissolved 170 g of 4-chloro-3-nitro-N-hexadecylbenzenesulfonamide obtained in the above step and after adding thereto 79 g of potassium carbonate, 6 ml of polyethylene glycol (average molecular weight: 400), and 71 g of dimethylsulfuric acid, the mixture was refluxed for 5 hours. To the reaction mixture was added 240 ml of acetone and after adding dropwise 870 ml of water to the mixture at 40° C., the mixture was cooled to room temperature, whereby crystals deposited. The crystals thus formed were recovered by filtration, washed with water and then methanol, and dried to provide 169 g of the above-described compound with a yield of 97%. The melting point thereof was 74° C. to 75° C.

Synthesis Example 2-5

Synthesis of Compound (4), 5-t-butyl-2-(4-N-methyl-N-hexadecylsulfamoyl-2-nitrophenyl)-4-isoxazolin-3-one:

After mixing 470 g of 4-chloro-3-nitro-N-methyl-N-hexadecylbenzenesulfonamide obtained in the above step, 169 g of 5-t-butyl-3-hydroxyisoxazole prepared in Synthesis Example 2-1, 168 g of potassium carbonate, and 1.2 liters of dimethyl sulfoxide, the reaction was performed for 6 hours at 65° C. The reaction mixture obtained was poured into ice-water and crystals thus deposited were recovered by filtration, washed with water, and dried to provide 576 g of the desired product with a yield of 100%. The melting point thereof was 67° C. to 68° C.

|  | Elemental Analysis: | | |
|---|---|---|---|
|  | C (%) | H (%) | N (%) |
| Calcd. | 62.15 | 8.52 | 7.23 |
| Found | 61.98 | 8.58 | 7.11 |

EXAMPLE 3

Synthesis of Compound (6), 5-t-butyl-2-(2-nitro-4-trifluoromethylphenyl)-4-isoxazolin-3-one:

After mixing 15.0 g of 4-chloro-3-nitrobenzotrifluoride, 11.3 g of 5-t-butyl-3-hydroxyisoxazole, 11.0 g of potassium carbonate, and 80 ml of dimethyl sulfoxide, the mixture was reacted for 4 hours at 80° C. After cooling, the reaction mixture obtained was poured into water to deposit crystals which were then recovered by filtration and recrystallized from a mixture of water and methanol to provide 10.0 g of the desired compound with a yield of 45.5%. The melting point thereof was 116° to 117° C.

|  | Elemental Analysis: | | |
|---|---|---|---|
|  | C (%) | H (%) | N (%) |
| Calcd. | 50.92 | 3.97 | 8.48 |
| Found | 51.11 | 4.05 | 8.47 |

EXAMPLE 4

Synthesis of Compound (7), 5-t-butyl-2-(4-ethoxycarbonyl-2-nitrophenyl)-4-isoxazolin-3-one:

In 100 ml of dimethyl sulfoxide were dissolved 23.0 g of ethyl 4-chloro-3-nitrobenzoate and 17 g of 5-t-butyl-3-hydroxyisoxazole and after adding thereto 17 g of potassium carbonate, the reaction was performed for 8 hours at 75° C. After the reaction was over, the reaction mixture obtained was poured into cold diluted hydrochloric acid followed by stirring, whereby colorless crystals deposited immediately. The crystals were recovered by filtration and recrystallized from ethanol to provide 31.7 g of the desired compound with a yield of 94.8%. The melting point thereof was 88° C.

|  | Elemental Analysis: | | |
|---|---|---|---|
|  | C (%) | H (%) | N (%) |
| Calcd. | 48.27 | 4.56 | 7.04 |
| Found | 48.25 | 4.55 | 7.09 |

EXAMPLE 5

Synthesis of Compound (8):

Synthesis Example 5-1

Synthesis of N-methyl-N-octadecyl-3-nitro-4-chlorobenzamide:

After adding 68.6 g of thionyl chloride to a mixture of 105.7 g of 3-nitro-4-chlorobenzoic acid and 800 ml of acetonitrile, the mixture was refluxed for 4 hours. After cooling the reaction mixture, the solvent was distilled off therefrom and the residue formed was dissolved in chloroform. To the solution was added 63.5 g of triethylamine and after adjusting the temperature thereof to 5° C., a chloroform solution of 148.6 g of N-methyloctadecylamine was added dropwise to the solution to perform reaction. After the reaction was over, water was added to the reaction mixture, and the organic phase thus formed was recovered and dried over anhydrous sodium sulfate. After filtering off inorganic materials, the solvent was distilled off from the filtrate and the residue was recrystallized from a 1:3 mixture of acetonitrile and methanol to provide 186 g of the desired compound with a yield of 76.0%. The melting point thereof was 55° C. to 56° C.

Synthesis Example 5-2

Synthesis of Compound (8), 5-t-butyl-2-(4-N-methyl-N-octadecylcarbamoyl-2-nitrophenyl)-4-isoxazolin-3-one:

After adding 300 ml of dimethylformamide to a mixture of 34.1 g of N-methyl-N-octadecyl-3-nitro-4-chlorobenzamide obtained in the above step, 12.4 g of 5-t-butyl-3-hydroxyisoxazole, and 12.4 g of potassium carbonate, the mixture was reacted for 5 hours at 100° C. The solvent was distilled off from the reaction mixture under reduced pressure and after adding ethyl acetate and water to the residue followed by stirring, the organic phase formed was recovered and applied to silica gel column chromatography to recover the main product which was then recrystallized from a mixture of n-hexane and ethyl acetate to provide 18.0 g of the above-described compound with a yield of 43.1%. The melting point thereof was 64° C.

| | Elemental Analysis: | | |
|---|---|---|---|
| | C (%) | H (%) | N (%) |
| Calcd. | 69.32 | 9.34 | 7.35 |
| Found | 69.21 | 9.24 | 7.25 |

EXAMPLE 6

Synthesis of Compound (9), 5-t-butyl-2-(4-ethoxycarbonyl-5-hexadecyloxy-2-nitrophenyl)-4-isoxazolin-3-one:

In 300 ml of dimethyl sulfoxide were dissolved 65 g of ethyl 4-chloro-2-hexadecyloxy-5-nitrobenzoate and 24 g of 5-t-butyl-3-hydroxyisoxazole and after adding thereto 24 g of potassium carbonate, the reaction was performed for 8 hours at 75° C. After the reaction was over, the reaction mixture obtained was poured into diluted hydrochloric acid and the product formed was extracted with ethyl acetate. After recovering and drying the organic phase thus formed, the solvent was distilled off from the organic phase and the residue thus formed was carefully applied to silica gel column chromatography, whereby the aforesaid compound was obtained as the main product. The product thus obtained was recrystallized from a mixture of methanol and acetonitrile to provide 30.1 g of the desired compound with a yield of 37.9%. The melting point thereof was 35° C. to 36° C.

| | Elemental Analysis: | | |
|---|---|---|---|
| | C (%) | H (%) | N (%) |
| Calcd. | 66.87 | 8.77 | 4.87 |
| Found | 66.59 | 8.87 | 4.69 |

EXAMPLE 7

Synthesis of Compound (10), 5-t-butyl 2-(4-nitrophenyl)-4-isoxazolin-3-one:

5.0 g of 4-fluoronitrobenzene, 5.0 g of 5-t-butyl-3-hydroxyisoxazole, 4.0 g of potassium t-butoxide, and 70 ml of toluene were mixed, and after adding 0.5 g of 1-(2-ethylhexyl)pyridinium chloride to the mixture, the resultant mixture was refluxed for 10 hours. The reaction mixture obtained was cooled and carefully applied to silica gel column chromatography to provide 0.6 g of the above-described compound with a yield of 6.5%. The melting point thereof was 125° C. to 127° C.

| | Elemental Analysis: | | |
|---|---|---|---|
| | C (%) | H (%) | N (%) |
| Calcd. | 59.54 | 5.38 | 10.68 |
| Found | 59.53 | 5.40 | 10.70 |

EXAMPLE 8

Synthesis of Compound (11), 5-t-butyl-2-(2,4-dinitrophenyl)-4-isoxazolin-3-one:

After mixing 3.7 g of 2,4-dinitrofluorobenzene, 20 ml of dimethylformamide, 2.9 g of 5-t-butyl-3-hydroxyisoxazole, and 2.8 g of potassium carbonate, the reaction was performed for 30 minutes at 80° C. and after cooling the reaction mixture, the product formed was extracted with a mixture of diethyl ether and ethyl acetate. The solvent was distilled off from the extract under reduced pressure and the residue obtained was crystallized from a mixture of diethyl ether and ethyl acetate to provide 1.9 g of the desired compound with a yield of 30.9%. The melting point thereof was 167° C. to 168° C.

| | Elemental Analysis: | | |
|---|---|---|---|
| | C (%) | H (%) | N (%) |
| Calcd. | 50.82 | 4.26 | 13.68 |
| Found | 50.59 | 4.41 | 13.67 |

EXAMPLE 9

Synthesis of Compound (12), 5-t-butyl-2-(4-nitro-3-trifluoromethylphenyl)-4-isoxazolin-3-one:

After mixing 15.0 g of 2-nitro-5-chlorobenzotrifluoride, 11.3 g of 5-t-butyl-3-hydroxyisoxazole, 11.0 g of potassium carbonate, and 80 ml of dimethyl sulfoxide, the reaction was performed for 6 hours at 100° C. After the reaction was over, the reaction mixture was poured into ice-water and then extracted with ethyl acetate. The organic phase formed was recovered and applied to silica gel column chromatography. The main product thus obtained was recrystallized from a mixture of methanol and water to provide 4.1 g of the desired compound with a yield of 18.7%. The melting point thereof was 125° C. to 126° C.

| | Elemental Analysis: | | |
|---|---|---|---|
| | C (%) | H (%) | N (%) |
| Calcd. | 50.92 | 3.97 | 8.48 |
| Found | 50.66 | 4.21 | 8.20 |

EXAMPLE 10

Synthesis of Compound (15), 5-t-butyl-2-(4-nitro-2-trifluoromethylphenyl)-4-isoxazolin-3-one:

After mixing 15 g of 2-chloro-5-nitrobenzotrifluoride, 11.3 g of 5-t-butyl-3-hydroxyisoxazole, 11.0 g of potassium carbonate, and 80 ml of dimethyl sulfoxide, the reaction was performed for 5 hours at 80° C. After the reaction was over, the reaction mixture was cooled and extracted with ethyl acetate and water. The organic phase thus formed was recovered and applied to silica gel column chromatography. The main product thus obtained was recrystallized from a mixture of methanol and water to provide 8.8 g of the desired product with a yield of 40.1%. The melting point thereof was 59° C. to 60° C.

| | Elemental Analysis: | | |
|---|---|---|---|
| | C (%) | H (%) | N (%) |
| Calcd. | 50.92 | 3.97 | 8.48 |
| Found | 50.72 | 4.22 | 8.19 |

EXAMPLE 11

Synthesis of Compound (17), 5-methyl-2-(4-dimethyl-sulfamoyl-2-nitrophenyl)-4-isoxazolin-3-one:

After mixing 27.9 g of diethyl 4-chloro-3-nitrobenzenesulfonamide, 11.9 g of 5-methyl-3-hydroxyisoxazole, 16.8 g of sodium hydrogencarbonate, and 120 ml of dimethyl sulfoxide, the reaction was performed for 6 hours at 70° C. The reaction was over, the reaction mixture obtained was poured into water, and crystals thus deposited were recovered and recrystallized from a mixture of methanol and water to provide 29.5 g of the desired product with a yield of 86.3%. The melting point thereof was 141° C. to 142° C.

| | Elemental Analysis: | | |
|---|---|---|---|
| | C (%) | H (%) | N (%) |
| Calcd. | 47.32 | 4.82 | 11.82 |
| Found | 47.37 | 4.82 | 11.85 |

EXAMPLE 12

Synthesis of Compound (21), 5-methyl-2-(4-N-methyl-N-hexadecylsulfamoyl-2-nitrophenyl)-4-isoxazolin-3-one:

After mixing 16 g of N-methyl-N-hexadecyl-4-chloro-3-nitrobenzenesulfonamide, 4.8 g of 3-hydroxy-5-methylisoxazole, 6.4 g of sodium hydrogencarbonate, and 48 ml of dimethyl sulfoxide, the reaction was performed for 6 hours at 75° C. The reaction was over, the reaction mixture formed was cooled, and after adding thereto 75 ml of methanol, 35 ml of water was slowly added dropwise to the mixture to deposit crystals which were then recovered by filtration and recrystallized from a 4:1 mixture of methanol and acetonitrile to provide 17.2 g of the desired compound with a yield of 95.1%. The melting point thereof was 63° C. to 65° C.

| | Elemental Analysis: | | |
|---|---|---|---|
| | C (%) | H (%) | N (%) |
| Calcd. | 60.30 | 8.06 | 7.81 |
| Found | 60.50 | 8.13 | 7.83 |

EXAMPLE 13

Synthesis of Compound (23), 5-methyl-2-(4-ethoxycarbonyl-2-nitrophenyl)-4-isoxazolin-3-one:

After mixing 400 g of ethyl 4-chloro-3-nitrobenzoate, 1.2 liters of dimethyl sulfoxide, 270 g of 5-methyl-3-hydroxyisoxazole, and 292 g of potassium carbonate, the reaction was performed for 10 hours at 60° C. After the reaction was over, the reaction mixture was poured into water and crystals thus deposited were recovered by filtration and recrystallized from ethyl acetate to provide 300.1 g of the desired compound with a yield of 59.0%. The melting point thereof was 122° C. to 123° C.

| | Elemental Analysis: | | |
|---|---|---|---|
| | C (%) | H (%) | N (%) |
| Calcd. | 53.43 | 4.14 | 9.59 |
| Found | 53.25 | 4.17 | 9.66 |

EXAMPLE 14

Synthesis of Compound (29), 5-t-butyl-2-(2,4-bismethanesulfonylphenyl)-4-isoxazolin-3-one:

After mixing 1 g of 2,4-bismethanesulfonylchlorobenzene, 1 g of 5-t-butyl-3-hydroxyisoxazole, 1 g of potassium carbonate, and 8 ml of dimethyl sulfoxide, the reaction was performed for 4 hours at 80° C. After the reaction was over, the reaction mixture obtained was poured into water and extracted with ethyl acetate. Then, the ethyl acetate was distilled off from the extract under reduced pressure and the residue thus formed was recrystallized from a mixture of water and methanol to provide 0.85 g of the desired compound with a yield of 61.2%. The melting point thereof was 166° C. to 168° C.

| | Elemental Analysis: | | |
|---|---|---|---|
| | C (%) | H (%) | N (%) |
| Calcd. | 48.24 | 5.12 | 3.75 |
| Found | 47.96 | 5.12 | 3.71 |

EXAMPLE 15

Synthesis of Compound (33), 5-t-butyl-2-(4-nitro-2-N-methyl-N-octadecylsulfamoylphenyl)-4-isoxazolin-3-one:

After mixing 62 g of N-methyl-N-octadecyl-2-chloro-5-nitrobenzenesulfonamide, 220 ml of dimethylformamide, 20.9 g of 5-t-butyl-3-hydroxyisoxazole, and 20.7 g of potassium carbonate, the reaction was performed for 6 hours at 80° C. After the reaction was over, the reaction mixture was acidified with hydrochloric acid and after distilling off the dimethylformamide from the reaction mixture, the product formed was extracted with water and ethyl acetate. The organic phase obtained was purified by silica gel column chromatography and the main product was recovered to provide 29 g of the desired product with a yield of 38.8%. The melting point thereof was 55° C. to 56° C.

| | Elemental Analysis: | | |
|---|---|---|---|
| | C (%) | H (%) | N (%) |
| Calcd. | 63.23 | 8.79 | 6.91 |
| Found | 63.30 | 8.84 | 6.88 |

EXAMPLE 16

Synthesis of Compound (38):

Synthesis Example 16-1

Synthesis of 5-(4-methoxyphenyl)-3-hydroxyisoxazole:

The compound was synthesized according to a modification of the method described in *Canadian Journal of Chemistry*, Vol. 62, 1940 (1984). That is, the reaction was performed by changing the reaction medium from water to a 1:1 mixture of water and ethanol, after the reaction was over, the reaction mixture was mixed with concentrated hydrochloric acid of the same volume as that of the reaction mixture, the mixture was refluxed for 5 hours, and after cooling the reaction mixture, crystals thus deposited were recovered by filtration.

The yield for the product was 41.8% and the melting point thereof was 191° C. to 193° C. (decompd.).

Synthesis Example 16-2

Synthesis of Compound (38), 5-(4-methoxyphenyl)-2-(2-nitro-4-trifluoromethylphenyl)-4-isoxazolin-3-one:

After mixing 20.0 g of 4-chloro-3-nitrobenzotrifluoride, 20.0 g of 5-(4-methoxyphenyl)-3-hydroxyisoxazole obtained in the above step, 16.0 g of potassium carbonate, and 120 ml of dimethyl sulfoxide, the reaction was performed for 6 hours at 60° C. After the reaction was over, the reaction mixture formed was poured into water and crystals thus deposited were recovered by filtration and recrystallized from a mixture of dimethylformamide and methanol to provide 30.5 g of the desired product. The melting point thereof was 170° C. to 171° C.

| | Elemental Analysis: | | |
|---|---|---|---|
| | C (%) | H (%) | N (%) |
| Calcd. | 53.69 | 2.92 | 7.37 |
| Found | 53.71 | 2.88 | 7.33 |

EXAMPLE 17

Synthesis of Compound (43):

Synthesis Example 17-1

Synthesis of 5-phenyl-3-hydroxyisoxazole:

The compound was synthesized according to the method described in *Chemical and Pharmaceutical Bulletin*, Vol. 14, No. 11, 1277–1286 (1966).

Synthesis Example 17-2

Synthesis of Compound (43), 5-phenyl-2-(4-N-methyl-N-octadecylsulfamoyl-2-nitrophenyl)-4-isoxazolin-3-one:

In 300 ml of dimethylformamide were dissolved 50.3 g of 2-nitro-4-N-methyl-N-octadecylsulfamoyl-1-chlorobenzene and 19.3 g of 5-phenyl-3-hydroxyisoxazole prepared in Synthesis Example 17-1 and after adding 16.8 g of potassium carbonate to the mixture, the reaction was performed for 5 hours at 80° C. After the reaction was over, the reaction mixture was filtered to remove inorganic materials and then after distilling off the solvent therefrom under reduced pressure, the residue obtained was crystallized from methanol to provide 52.2 g of the above-described compound with a yield of 83.2%. The melting point thereof was 93° C. to 94° C.

| | Elemental Analysis: | | |
|---|---|---|---|
| | C (%) | H (%) | N (%) |
| Calcd. | 65.04 | 7.87 | 6.69 |
| Found | 64.89 | 7.67 | 6.56 |

EXAMPLE 18

Synthesis of Compound (45), 5-phenyl-2-(4-N-methyl-N-hexadecylsulfamoyl-2-nitrophenyl)-4-isoxazolin-3-one:

After mixing 300 g of N-methyl-N-hexadecyl-4-chloro-3-nitrobenzenesulfonamide, 122 g of 5-phenyl-3-hydroxyisoxazole, 800 g of dimethyl sulfoxide, and 106 g of potassium carbonate, the reaction was performed for 7 hours at 60° C. After the reaction was over, the reaction mixture was cooled and poured into water. Crystals thus deposited were recovered by filtration, washed with water and then methanol, and dried to provide 376 g of the desired product with a yield of 99.3%. The melting point thereof was 88° C. to 89° C.

| | Elemental Analysis: | | |
|---|---|---|---|
| | C (%) | H (%) | N (%) |
| Calcd. | 64.08 | 7.56 | 7.00 |
| Found | 63.99 | 7.55 | 6.94 |

EXAMPLE 19

Synthesis of Compound (41), 5-(4-acetylaminophenyl)-2-(2-nitro-4-trifluoromethylphenyl)-4-isoxazolin-3-one:

After mixing 6.4 g of 4-chloro-3-nitrobenzotrifluoride, 7.0 g of 5-(4-acetylaminophenyl)-3-hydroxyisoxazole, 4.5 g of potassium carbonate, and 50 ml of dimethyl sulfoxide, the reaction was performed for 5 hours at 70° C. After the reaction was over, the reaction mixture obtained was poured into water and crystals thus formed were recovered by filtration and recrystallized from a mixture of dimethylformamide and methanol to provide 8.8 g of the desired product with a yield of 75.9%. The melting point thereof was 238° C. to 239° C.

| | Elemental Analysis: | | |
|---|---|---|---|
| | C (%) | H (%) | N (%) |
| Calcd. | 53.08 | 2.97 | 10.32 |
| Found | 53.13 | 3.00 | 10.51 |

EXAMPLE 20

Synthesis of Compound (50), 5-phenyl-(4-ethoxycarbonyl-2-nitrophenyl)-4-isoxazolin-3-one:

After mixing 200 g of ethyl 4-chloro-3-nitrobenzoate, 500 ml of dimethyl sulfoxide, 169 g of 5-phenylisoxazole, and 146 g of potassium carbonate, the reaction was performed for 5 hours at 60° C. After the reaction was over, the reaction mixture was cooled and poured into water to deposit crystals which were then recovered, washed with water, and dried to provide 292 g of the desired product with a yield of 94.6%. The melting point thereof was 142° C. to 143° C.

| | Elemental Analysis: | | |
|---|---|---|---|
| | C (%) | H (%) | N (%) |
| Calcd. | 61.02 | 7.90 | 7.91 |
| Found | 60.95 | 8.10 | 7.88 |

EXAMPLE 21

Synthesis of Compound (51), 5-phenyl-2-(2-nitro-4-trifluoromethylphenyl)-4-isoxazolin-3-one:

After mixing 22.6 g of 4-chloro-3-nitrobenzotrifluoride, 19.3 g of 5-phenyl-3-hydroxyisoxazole, 16.8 g of potassium carbonate, and 150 ml of dimethyl sulfoxide, the reaction was performed for 3 hours at 70° C. After the reaction was over, the reaction mixture was cooled and poured into water. Crystals thus deposited were recovered by filtration and recrystallized from a mixture of dimethylformamide and methanol to provide 28.4 g of the desired product with a yield of 95.0%. The melting point thereof was 185° C. to 187° C.

| | Elemental Analysis: | | |
|---|---|---|---|
| | C (%) | H (%) | N (%) |
| Calcd. | 54.87 | 2.59 | 8.00 |
| Found | 54.57 | 2.51 | 7.77 |

EXAMPLE 22

Synthesis of Compound (27), 5-t-butyl-2-(4-methanesulfonyl-2-tetradecylsulfonylphenyl)-4-isoxazolin-3-one:

After mixing 32 g of 4-methanesulfonyl-2-tetradecylsulfonylchlorobenzene, 20 g of 5-t-butyl-3-hydroxyisoxazole, 20 g of potassium carbonate, and 140 ml of dimethyl sulfoxide, the reaction was performed for 4 hours at 80° C. After the reaction was over, the reaction mixture formed was poured into water and extracted with ethyl acetate. The organic phase obtained was purified by silica gel column chromatography and 20.0 g of the desired compound was obtained as the main product with a yield of 50.8%. The melting point thereof was 85° C. to 86° C.

| | Elemental Analysis: | | |
|---|---|---|---|
| | C (%) | H (%) | N (%) |
| Calcd. | 60.51 | 8.16 | 2.52 |
| Found | 60.50 | 8.10 | 2.50 |

Examples of synthesizing positive working compounds for silver halide photographic materials using the compounds of this invention described above are shown by the following Reference Examples.

Reference Example 1-1

Synthesis of 4-chloromethyl-5-t-butyl-2-(4-N-methyl-N-octadecylcarbamoyl-2-nitrophenyl)-4-isoxazoline-3-one:

After mixing 36 g of 5-t-butyl-2-(4-N-methyl-N-octadecylcarbamoyl-2-nitrophenyl)-4-isoxazolin-3-one, 5.7 g of paraformaldehyde, 10.3 g of zinc chloride, and 250 ml of acetic acid, the reaction was performed for 20 hours at 100° C. while blowing hydrogen chloride gas into the reaction system. After the reaction was over, the reaction mixture was cooled and poured into ice-water. Solids thus deposited were recovered by filtration, dissolved in chloroform, and purified by column chromatography to provide 10.1 g of the above-described compound with a yield of 25.6%. The melting point thereof was 77° C.

Reference Example 1-2

Synthesis of 4-(4-t-butoxycarbonylaminophenoxy)-methyl-5-t-butyl-2-(4-N-methyl-N-octadecylcarbamoyl-2-nitrophenyl)-4-isoxazolin-3-one:

After mixing 10.0 g of 4 chloromethyl-5-t-butyl-2-(4-N-methyl-N-octadecylcarbamoyl-2-nitrophenyl)-4-isoxazolin-3-one prepared in Reference Example 1-1, 4.0 g of 4-t-butoxycarbonylaminophenol, 3.0 g of potassium carbonate, and 100 ml of acetone, the mixture was refluxed for 7 hours. After the reaction was over, the acetone was distilled off from the reaction mixture and the product formed was extracted with ethyl acetate and water. The organic phase thus obtained was purified by silica gel column chromatography to provide 9.0 g of the desired product with a yield of 70.5%.

Reference Example 1-3

Synthesis of 4-(4-aminophenoxy)methyl-5-t-butyl-2-(4-N-methyl-N-octadecylcarbamoyl-2-nitrophenyl)-4-isoxazolin-3-one:

In 100 ml of chloroform was dissolved 9.0 g of 4-(4-t-butoxycarbonylaminophenoxy)methyl-5-t-butyl-2-(4-N-methyl-N-octadecylcarbamoyl-2-nitrophenyl)-4-isoxazolin-3-one prepared in Reference Example 1-2 and after cooling the solution below 5° C., 10 ml of trifluoroacetic acid was slowly added dropwise to the solution. Then, the mixture was allowed to gradually raise the temperature to room temperature and the reaction was performed for 10 hours at that temperature. After the reaction was over, the reaction mixture obtained was poured into an aqueous sodium bicarbonate solution to neutralize it and extracted with ethyl acetate. The extract was purified by silica gel flash column chromatography to provide 6.9 g of the desired product with a yield of 90.8%.

Reference Example 1-4

Synthesis of Positive Working Compound A:

In 40 ml of chloroform was dissolved 5.4 g of 4-(4-aminophenoxy)methyl-5-t-butyl-2-(4-N-methyl-N-octadecylcarbamoyl-2-nitrophenyl)-4-isoxazolin-3-one prepared in Reference Example 1-3 and the solution obtained was cooled to 0° C. Then, 0.8 g of pyridine was added to the solution and after adding thereto 3.1 g of Compound A shown below, they mixture was reacted for 2 hours.

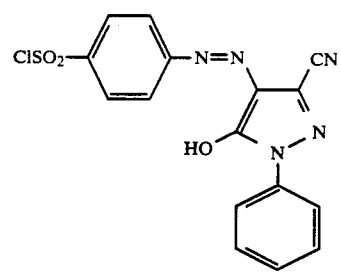

Compound A:

After the reaction was over, the chloroform was distilled off from the reaction mixture, the residue formed was dissolved in a small amount of dimethylformamide and after adding thereto methanol to an extent of not depositing oily matters, the mixture was stirred, whereby crystals deposited. The crystals were recovered by filtration and purified again by the same way as above to provide 3.9 g of Positive Working Compound A shown below with a yield of 46.5%. The melting point thereof was 157° C. to 159° C.

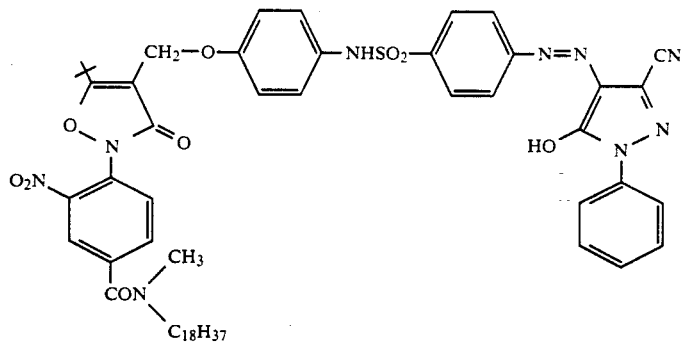

While the invention has been described in detail and with reference to specific embodiments thereof, it will be apparent to one skilled in the art that various changes and modifications can be made therein without departing from the spirit and scope thereof.

What is claimed is:

1. A compound of formula (I)

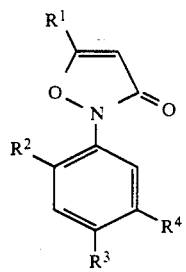

wherein $R^1$ represents an unsubstituted alkyl group having from 1 to 6 carbon atoms, an alkyl group having 1 to 6 carbon atoms which is substituted with chlorine, N-methylacetylamino or octylthio, an unsubstituted aryl having from 6 to 24 carbon atoms, or an aryl having from 6 to 24 carbon atoms which is substituted with methyl, methoxy, 3-methoxy-4-acetamido, 4-dodecycloxy, 4-octadecyloxy or 3-sulfo-4-methoxy; $R^2$, $R^3$ and $R^4$ are the same or different, each represents hydrogen or represents a sulfamoyl, a sulfamoyl substituted with an alkyl having from 1 to 18 carbon atoms, bis(2-methoxyethyl)-sulfamoyl, an alkoxycarbonyl having from 1 to 16 carbon atoms, an alkoxy having from 1 to 16 carbon atoms, an alkylsulfonyl having from 1 to 14 carbon atoms, a phenylsulfonyl, a phenylcarbonyl, an alkylcarbonyl having from 1 to 12 carbon atoms, a carbamoyl, a nitro, a cyano, a trifluoromethyl or a chloro, with the proviso that at least one of said $R^2$ and $R^3$ is trifluormethyl, nitro, cyano, an unsubstituted alkylsulfonyl, an alkylsulfonyl which is substituted with chlorine, a phenylsulfonyl or a phenylsulfonyl which is substituted with methyl.

2. The compound as claimed in claim 1, wherein at least one of $R^2$ and $R^3$ is nitro.

3. The compound as claimed in claim 1, wherein $R^2$ and $R^3$ each is trifluormethyl, cyano or an unsubstituted alkylsulfonyl, an alkylsulfonyl substituted with chlorine, a phenylsulfonyl, or a phenylsulfonyl which is substituted with methyl.

4. The compound as claimed in claim 1, wherein at least one of $R^2$, $R^3$, and $R^4$ is an unsubstituted alkylsulfonyl, an alkylsulfonyl substituted with chlorine, a phenylsulfonyl, or a phenylsulfonyl which is substituted with methyl, a sulfamoyl, an alkoxycarbonyl, a carbamoyl, trifluormethyl or a cyano.

5. The compound as claimed in claim 1, wherein $R^2$ is a nitro, $R^3$ is a sulfamoyl, a carbamoyl, an alkoxycarbonyl or trifluoromethyl, and $R^4$ is hydrogen. phenylsulfonyl or a phenylsulfonyl which is substituted with methyl.

6. The compound of claim 1, wherein said sulfamoyl is selected from the group consisting of dimethylsulfamoyl, diethylsulfamoyl, n-hexadecylsulfamoyl, N-methyl-N-n-hexadecylsulfamoyl, N-methyl-N-n-octadecylsulfamoyl, dihexylsulfamoyl, n-methyl-N-n-hexylsulfamoyl, methyloctylsulfamoyl, dibutylsulfamoyl, dioctylsulfamoyl and bis(2-methoxyethyl)-sulfamoyl.

7. The compound of claim 1, wherein said alkoxycarbonyl is ethoxycarbonyl.

8. The compound of claim 1, wherein said alkoxy is n-hexadecyloxy.

9. The compound of claim 1, wherein said alkylsulfonyl is selected from the group consisting of n-tetradecylsulfonyl, methylsulfonyl and n-dodecylsulfonyl.

10. The compound of claim 1, wherein at least one of $R^2$, $R^3$ and $R^4$ is phenylcarbonyl.

* * * * *